United States Patent [19]

Huth et al.

[11] 4,186,129
[45] Jan. 29, 1980

[54] 5-(SUBSTITUTED PHENYL)-OXAZOLIDINONES AND THEIR SULFUR ANALOGS

[75] Inventors: Andreas Huth; Ralph Schmiechen; Wolfgang Kehr; Gert Paschelke; Helmut Wachtel; Herbert H. Schneider; Dieter Palenschat, all of Berlin, Fed. Rep. of Germany

[73] Assignee: Schering Aktiengesellschaft, Berlin and Bergkamen, Fed. Rep. of Germany

[21] Appl. No.: 855,867

[22] Filed: Nov. 30, 1977

[30] Foreign Application Priority Data

Dec. 3, 1976 [DE] Fed. Rep. of Germany ....... 2655369

[51] Int. Cl.² .................. C07D 263/38; C07D 263/46; C07D 277/34; A61K 31/42
[52] U.S. Cl. .................................... 548/186; 424/270; 424/272; 548/188; 548/229; 548/230; 548/231; 548/232; 260/245.5; 260/243.3; 544/369; 544/133; 544/137; 544/121
[58] Field of Search .................... 260/307 C, 306.7 R, 260/306.7 C; 424/272, 270

Primary Examiner—Jose Tovar
Attorney, Agent, or Firm—Millen & White

[57] ABSTRACT

Novel 5-(substituted phenyl)-oxazolidinones and their sulfur analogs of Formula I

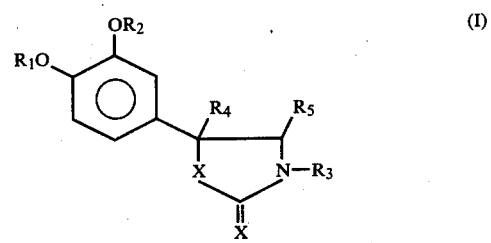

wherein
$R_1$ is optionally substituted lower alkyl, cycloalkyl or cycloalkylalkyl;
$R_2$ is hydrogen, optionally substituted lower alkyl, cycloalkyl, cycloalkylalkyl, optionally substituted aryl, optionally substituted aralkyl, alkenyl or a heterocyclic group;
$R_3$ is hydrogen, optionally substituted lower alkyl, alkenyl, alkynyl, optionally substituted aryl, optionally substituted aralkyl, or optionally substituted acyl;
$R_4$ is hydrogen or optionally substituted lower alkyl;
$R_5$ is hydrogen or optionally substituted lower alkyl or optionally substituted lower alkoxycarbonyl; and
X is oxygen or sulfur, have valuable pharmacological effects.

29 Claims, No Drawings

5-(SUBSTITUTED PHENYL)-OXAZOLIDINONES AND THEIR SULFUR ANALOGS

SUMMARY OF INVENTION

In a composition aspect, this invention provides novel 5-(substituted phenyl)-oxazolidinones and their sulfur analogs of Formula I

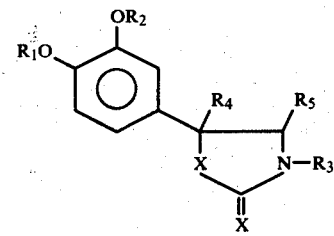

wherein
- $R_1$ is optionally substituted lower alkyl, cycloalkyl or cycloalkylalkyl;
- $R_2$ is hydrogen, optionally substituted lower alkyl, cycloalkyl, cycloalkylalkyl, optionally substituted aryl, optionally substituted aralkyl, alkenyl or a heterocyclic group;
- $R_3$ is hydrogen, optionally substituted lower alkyl, alkenyl, alkynyl, optionally substituted aryl, optionally substituted aralkyl, or optionally substituted acyl;
- $R_4$ is hydrogen or optionally substituted lower alkyl;
- $R_5$ is hydrogen or optionally substituted lower alkyl or optionally substituted lower alkoxycarbonyl; and
- X is oxygen or sulfur.

In a method of use aspect, this invention provides a method for achieving CNS-depressive, antidopaminergic, antinociceptive and anticonvulsive effects in mammals including humans and for treating diseases which involve a disturbance in the metabolism of cyclic nucleotides which comprises administering an amount of a compound of Formula I effective for such achievement of effects or such treatment.

DETAILED DISCUSSION

The compounds of Formula I possess an asymmetrical carbon atom and thus can be prepared as racemates as well as optical antipodes.

Lower alkyl and the lower alkyl moiety in the term "lower alkoxycarbonyl" include lower alkyl groups of up to 6 carbon atoms. Suitable such groups include methyl, ethyl, propyl, isopropyl, butyl, isobutyl, tert-butyl, pentyl, 2-methylbutyl, 2,2-dimethylpropyl, and hexyl. Suitable alkenyl and alkynyl groups are preferably those having from 2-5 carbon atoms, for example, 1-propenyl, 2-propenyl, 3-methyl-2-propenyl, vinyl, and propargyl.

All such lower alkyl groups can also be mono- or polysubstituted, e.g. by halogen, especially fluorine, chlorine, and bromine. Suitable such halogen-substituted alkyl groups include 2-chloroethyl, 3-chloropropyl, 4-bromobutyl, difluoromethyl, trifluoromethyl, 1,1,2-trifluoro-2-chloroethyl, 3,3,3-trifluoropropyl, 2,2,3,3,3-pentafluoropropyl, 1,1,1,3,3,3-hexafluoro-2-propyl. Other suitable substituents for the alkyl groups include hydroxy groups, e.g. forming 2-hydroxyethyl or 3-hydroxypropyl; carboxy groups, e.g. forming carboxymethyl or carboxyethyl; and alkoxy groups, wherein each alkoxy group can contain 1-5 carbon atoms, e.g. forming ethoxymethyl, isopropoxymethyl, 2-methoxyethyl, 2-isopropoxyethyl, 2-butoxyethyl, 2-isobutoxyethyl and 3-pentoxypropyl. The alkoxy groups, however, can also be ring-closed, forming cyclic ether residues, such as, for example, the 3-tetrahydropyranyl residue.

The lower alkyl groups can also be terminally substituted by amino groups wherein the nitrogen can optionally be mono- or disubstituted by alkyl groups of preferably 1-5 carbon atoms, or wherein the nitrogen forms part of a 4- to 7-membered ring. Suitable such N-substituted alkyl groups include aminomethyl, 2-methylaminoethyl, 2-dimethylaminoethyl, 2-diethylaminoethyl, 3-dimethylaminopropyl, 3-ethylmethylaminopropyl, 2-pyrrolidino ethyl, N-methylpiperazino ethyl, hexamethylenimino ethyl, etc.

Suitable cycloalkyl and cycloalkylalkyl groups preferably contain 3-7 carbon atoms. Preferred are the cyclopropyl, cyclopropylmethyl, cyclopentyl, and cyclohexyl groups.

Suitable aryl groups include phenyl and naphthyl. Suitable aralkyl groups include such aryl groups bonded to $C_{1-4}$ alkyl moieties. Suitable substituents for such aryl and aralkyl groups include those listed above for the lower alkyl groups. These substituents can be on either the aryl or alkyl portions. Other suitable substituents for the aryl portion of these moieties include $NO_2$, $C_{1-6}$ alkyl and $CF_3$.

Suitable heterocyclic groups for $R_2$ include $C_{4-7}$ aliphatic heterocyclic groups containing one O, N or S atom such as 2- or 3-tetrahydrofuranyl, 2- or 3-tetrahydrothienyl, 2-tetrahydropyranyl and heterocyclic aromatic groups containing one O, N or S atom and from 5-9 carbon atoms.

Suitable acyl groups include all residues of physiologically compatible carboxylic acids, e.g. hydrocarbon carboxylic acids. Preferred are alkanoyl groups derived from acids of 1-18 carbon atoms, preferably 2-8 carbon atoms, such as, for example, monobasic acyclic aliphatic carboxylic acids such as formic, acetic, propionic, butyric, isobutyric, a-ethylbutyric, pivalic, valeric, isovaleric, α-ethylvaleric, trimethylacetic, 2-methylbutyric, 3-ethylbutyric, caproic, triethylacetic, enanthic, or caprylic acid; or cyclic acids, perferably cycloaliphatic acids, such as cyclopropylideneacetic, cyclobutylcarboxylic, cyclopentylcarboxylic, cyclopentylacetic, β-cyclopentylpropionic, cyclohexylcarboxylic, or cyclohexylacetic acid. Aroyl groups are also suitable and are derived from carbocyclic aryl, alkaryl or aralkyl acids, such as benzoic acid or 2-, 3-, or 4-methylbenzoic acid. Aryl and aralkyl are as defined above including the substituted versions thereof which include the alkaryl group.

Since the chemical character of the acyl group is not critical for the properties of the compounds of this invention, as long as the acyl group does not have a toxic effect, it is suitable for use in this invention. Thus, also suitable are all such acyl groups derived from aliphatic, araliphatic, and aromatic, acyclic and cyclic (carbo- and hetero-cyclic), unsubstituted and substituted, hydrocarbon and non-hydrocarbon (e.g., having O, S or N atoms), saturated and unsaturated, mono-, di-, and polybasic carboxylic acids of up to 18 carbon atoms, preferably up to 8 carbon atoms.

Suitable acids in this connection include undecylic, dodecanoic, tetradecanoic, hexadecanoic, octadecanoic, palmitic, stearic, and β-cyclohexylpropionic acid; 2,3-, 2,4-, 2,6-, 3,4-, and 3,5- dimethylbenzoic, ethyl benzoic, naphthoic, 3-methyl-α-naphthoic, β-phenylpropionic, diphenylacetic, and α-naphthylacetic acid; carbamic acids, such as carbamic, phenylcarbamic, n-butylcarbamic, dimethylcarbamic, diethylcarbamic, and allophanic acid; and heterocyclic acids, such as β-furylcarboxylic, pyrrolecarboxylic, β-pyrrolidinopropionic, N-methylpyrrolidino-2-carboxylic, 6-hydroxy-indolyl-3-acetic, N-methylmorpholino-2-carboxylic, and pyrrole-2-carboxylic acid. As stated, the acyl residues can optionally be mono- or polysubstituted. Suitable substituents include the following: hydroxy, halo, alkyl, alkoxy, carboxy, aralkoxy, acyloxy, sulfonyloxy, amido, sulfato, nitro, mercapto, and cyano wherein aryl, alkyl and acyl are as defined herein.

Thus, suitable acyl residues include those from glycolic, lactic, citric, tartaric, maleic, glyceric, mannonic, gluconic, and salicylic acid; or from amino acids, such as glycine, aminopropionic, diglycolamino triglycolamino, methylglycine, dimethylglycine and diethylglycine acid. Also suitable are the acyl residues of p-amino-salicylic, p-aminobenzoic, ethylmercaptoacetic, benzylmercaptoacetic, chloroacetic, fluoroacetic, trichloroacetic, trifluoroacetic, thioglycolic, m-nitrobenzoic, 2,3,4-trimethoxybenzoic, phenoxyacetic, and α-naphthyloxyacetic acid; as well as the alkoxylated and aralkoxylated acyl residues of formic acid, such as, for example, carbethoxy and carbobenzyloxy.

The compounds of Formula I may be prepared by fully conventional methods. For example, 2-amino-1-(3,4-disubstituted phenyl)-ethanols of general Formula II

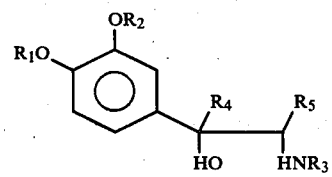

wherein $R_{1-5}$ are as defined above, can be reacted in a conventional manner in an inert solvent, in the presence of an alkaline catalyst, while heating, with a carbonic acid derivative or a thiocarbonic acid derivative of Formula III

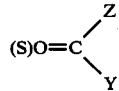

wherein

Z and Y are each OR, chlorine, bromine, or imidazole (R being alkyl, aryl, aralkyl, or when Z and Y are taken together, alkylene).

The resultant compound of formula I can be converted to others of Formula I by optionally thereafter splitting off any araliphatic ether group reductively with Raney nickel or with a noble metal catalyst; and-/or alkylating any free hydroxy group; and/or exchanging the ring oxygen and/or the oxygen of the 2-carbonyl group with sulfur; and/or if $R_3$ is hydrogen, N-acylating or N-alkylating (and also adding aryl, alkenyl, alkynyl and aralkyl groups to the N atom).

The starting material of Formula II can be prepared by fully conventional procedures, for example, as shown in Example I herein, from simple starting materials such as appropriately substituted aminoethanols and appropriately substituted benzaldehydes. The carbonic acid derivatives of Formula III are also fully conventional (e.g., L. F. and M. Fieser, Reagents for Organic Synthesis, John Wiley & Sons, Inc., N.Y., 1967, pp. 114 resp. 247).

The ring closure reaction in the compounds of Formula II can in fact be conducted with all carbonic acid or thiocarbonic acid derivatives of Formula III. R can be identical or different for Z and Y and includes lower alkyl or aralkyl, such as, for example, methyl, ethyl, and benzyl. However, R can also be an alkylene residue, such as, for example, propylene or isobutylene. The nature of the R group is not critical and, for example, the alkyl, aryl, and aralkyl groups discussed above are suitable. This ring closure reaction is disclosed for example in the U.S. Pat. No. 2,399,188.

The solvents utilized are advantageously inert with respect to the reactants. Suitable such solvents include ethers, such as diethyl ether, glycol dimethyl ether, or diethylene glycol dimethyl ether; aliphatic and aromatic hydrocarbons, such as hexane, benzene, toluene, xylene, and mesitylene; alcohols, such as methanol, ethanol, propanol, butanol; as well as dimethyl sulfoxide, glycol monomethyl ether, and diethylene glycol monomethyl ether.

The reaction is suitably conducted while heating. Suitable temperatures are above room temperature and can range up to the boiling point of the reaction mixture, wherein the temperature range of 60°–200° C., preferably 100°–160° C. is typical.

The cyclization reaction is effected in the presence of an alkaline catalyst. Suitable alkaline catalysts include alkali metal and alkaline earth metal carbonates and particularly alcoholates, such as sodium methylate and potassium carbonate. However, likewise suitable are organic bases, such as pyridine, triethylamine, and alkali metal and alkaline earth metal hydroxides, e.g. sodium hydroxide, especially when Z or Y is a halogen. When Z and Y are both halogen, such as chlorine, for example, the addition of a basic catalyst can be omitted. If Z and Y represent imidazole residues, the process is preferably conducted at room temperature, suitable solvents being dimethylformamide, tetrahydrofuran, and methylene chloride.

The optional subsequent reductive splitting of an araliphatic ether group, such as splitting off of the benzyl group, can be accomplished with any conventional, metal catalysts for the purpose, such as, for example, platinum, palladium, rhodium, or nickel, in their pure forms as well as on support meterials, such as carbon, calcium carbonate, and barium sulfate. Suitable solvents include all those which are inert with respect to the reducing agents under the conditions of this invention. Examples in this connection are organic acids, such as acetic acid and propionic acid; lower alcohols, such as methanol and ethanol; esters, such as ethyl acetate; and aliphatic, cycloaliphatic, and aromatic hydrocarbons, such as hexane, cyclohexane, and benzene.

The optional subsequent O-alkylation (i.e., if $R_3$ is hydrogen) likewise takes place according to conventional methods. The alkylation is preferably conducted with the corresponding $R_3$ halide, mesylate or tosylate. Suitable halogenides are the chlorides, bromides, and iodides. For purposes of alkylation, the hydroxy compound of Formula I is dissolved, for example, in a polar solvent and heated in the presence of a base with the alkylating agent to temperatures of between 30° and 150° C. Suitable bases include, for example, sodium hydride, potassium carbonate and alkali alcoholates, such as sodium ethylate, potassium butylate, and potassium tert-butylate. Suitable solvents include dimethylformamide, dimethylacetamide, hexamethylphosphoric triamide, acetonitrile, dimethyl sulfoxide, tetrahydrofuran, dioxane, ketones, such as acetone and methyl isobutyl ketone, as well as alcohols, such as ethanol, butanol, and tert-butanol.

The exchange of the carbonyl oxygen or of the ring oxygen in compounds of Formula I with sulfur is conducted according to conventional methods, e.g. according to the method of Scheeren et al., Synthesis (1973):149.

For this purpose, suitable reactants include polysulfides, such as phosphorus pentasulfide, in a solvent or solvent mixture in the presence of a base. The reaction can also be accomplished in a suspension. Suitable solvents or suspension agents include, for example, acetonitrile, tetrahydrofuran, diethyl ether, glycol dimethyl ether, and pyridine. Suitable bases are sodium bicarbonate, potassium carbonate, etc. The reaction is terminated at 30°–120° C. after about 3–24 hours.

The optional subsequent N-acylation or N-alkylation ($R_3$=H) also can be carried out according to conventional methods. For example, the compound of Formula I can be dissolved in a polar solvent and heated to 40°–150° C. with an alkyl or aryl or acyl halogenide or an acyl anhydride in the presence of a salt-forming agent.

Suitable polar solvents include dimethylformamide, dimethylacetamide, tetrahydrofuran, dioxane, as well as alcohols, such as ethanol and butanol. Suitable salt-forming agents include, for example, sodium hydride, potassium carbonate, alkali alcoholates, such as sodium ethylate, potassium tert-butylate, etc. The reaction with haloaryl groups, e.g. iodobenzene, can also be conducted without solvents, preferably in the presence of copper powder.

The compounds of Formula I of this invention possess valuable pharmacological properties. They exhibit CNS-depressive, antidopaminergic, antinociceptive, and anticonvulsive effects. Thus, they have a certain similarity to neuroleptics, such as chlorpromazine or haloperidol. The compounds of this invention, however, differ from the classical neuroleptics since they exert a different influence on receptor-dependent, monoaminergic feedback mechanisms, i.e., a reduction of extrapyramidal side effects.

Furthermore, the compounds of this invention possess strong phosphodiesterase-inhibiting properties and thus affect the metabolism of cyclic nucleotides.

On the basis of the aforedescribed effects, the compounds of this invention can be utilized in the form of pharmaceutical preparations for the treatment of the aforementioned diseases. Conventional excipients are pharmaceutically acceptable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salt for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 0.05–50 mg. in a pharmaceutically acceptable carrier per unit dosage.

For oral administration, the amount of active agent per oral dosage unit usually is 1–50 mg., preferably 5–25 mg. The daily dosage is usually 1–100 mg., preferably 10–50 mg. p.o. For parenteral application, the amount of active agent per dosage unit is usually 0.05–20 mg., preferably 0.1–10 mg. The daily dosage is usually 0.1–50 mg., preferably 0.2–10 mg. i.v. or i.m.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The temperatures in the examples are set forth in degrees Celsius.

EXAMPLE 1

5-(3-Benzyloxy-4-methoxyphenyl)-2-oxazolidinone 318.6 millimoles of 3-benzyloxy-4-methoxybenzaldehyde is dissolved in 1200 ml. of ether. A solution of 558 mmol potassium cyanide in 300 ml. of water is added at room temperature to the reaction mixture. After cooling to 0°, 237 mmol 2 N sulfuric acid is added dropwise to the thoroughly stirred mixture, and the latter is agitated for 12 hours at room temperature. After separation of the aqueous phase, the ether is washed repeatedly with 50 ml. of semisaturated NaCl solution and high-dried over calcium chloride. After the mixture has been filtered off from the desiccant and washed twice with 100 ml. of ether, the combined organic phases, which contain the crude 2-(3-benzyloxy-4-methoxyphenyl)-2-hydroxyacetonitrile, are utilized in the next stage.

Analogously, with 3,4-dimethoxybenzaldehyde as the starting material, 2-(3,4-dimethoxyphenyl)-2-hydroxyacetonitrile is produced, and from 3-cyclopentoxy-4-methoxybenzaldehyde as the starting material, 2-(3-cyclopentoxy-4-methoxyphenyl)-2-hydroxyacetonitrile is obtained.

1.3 mol of lithium aluminum hydride is suspended in incremental portions in 1 liter of absolute ether; under cooling and thorough agitation, an ether solution of 2-(3-benzyloxy-4-methoxyphenyl)-2-hydroxyacetonitrile is added dropwise to the reaction mixture so that only a slight reflux occurs. After agitation at room temperature overnight, the mixture is cooled and first 400 ml. of ethyl acetate and then 600 ml. of water are added dropwise. The mixture is then vacuum-filtered from the thus-produced precipitate, and the residue is washed twice with respectively 200 ml. of ethanol:water (1:1). The collected filtrates are greatly concentrated and taken up in 300 ml. of semiconcentrated hydrochloric acid. This solution is extracted twice with respectively 200 ml. of ethyl acetate. The ethyl acetate phase is discarded, and the hydrochloric solution is cooled and rendered alkaline with potassium hydroxide solution—any thus-precipitated aluminum salts are removed by vacuum filtration—and then extracted three times with respectively 400 ml. of ether. The combined organic phases are dried, concentrated after filtration, and recrystallized from ethyl acetate.

The final product, obtained in a 20% yield, namely 2-amino-1-(3-benzyloxy-4-methoxyphenyl)-ethanol melts at 101°-102°.

Analogously, 2-(3,4-dimethoxyphenyl)-2-hydroxyacetonitrile produces a 49% yield of 2-amino-1-(3,4-dimethoxyphenyl)-ethanol (m.p. 80°-81°, benzene); and 2-(3-cyclopentoxy-4-methoxyphenyl)-2-hydroxyacetonitrile produces a 70% yield of 2-amino-1-(3-cyclopentoxy-4-methoxyphenyl)-ethanol (oil).

2-Amino-1-(3-benzyloxy-4-methoxyphenyl)-ethanol can also be prepared as follows:

50 mmol of 3-benzyloxy-4-methoxybenzaldehyde and 55 mmol of trimethylsilyl cyanide are heated together with 0.567 mmol of anhydrous zinc iodide for 4 hours under nitrogen and exclusion of moisture to 90°. The mixture is then taken up in 15 ml. of absolute tetrahydrofuran, and this solution is added dropwise to a suspension of 60 mmol of lithium aluminum hydride in 35 ml. of tetrahydrofuran. After heating the mixture for one hour to 60°, it is worked up as described in Example 1. Recrystallization from ethyl acetate produces 2-amino-1-(3-benzyloxy-4-methoxyphenyl)-ethanol, m.p. 100°-102°, in a 30% yield.

36 mmol of 2-amino-1-(3-benzyloxy-4-methoxyphenyl)-ethanol is suspended with 50 mmol of sodium methylate and 91.4 mmol of diethyl carbonate in 120 ml. of absolute toluene and heated under the exclusion of moisture for 2 hours to a bath temperature of 110°, and during this step methanol and ethanol pass over through distillation. The toluene is thereafter distilled off, during the last stage under an oil pump vacuum. The residue is taken up in 150 ml. of chloroform and distributed over 100 ml. of water. The aqueous phase is extracted twice with respectively 150 ml. of chloroform; the combined chloroform extracts are washed with 100 ml. of water, dried, filtered, concentrated, and recrystallized from ethyl acetate, thus obtaining 5-(3-benzyloxy-4-methoxyphenyl)-2-oxazolidinone, m.p. 132°-133° (91% yield).

EXAMPLE 2

Analogously to Example 1, the oxazolidinones listed in the following table are produced from the corresponding amino alcohols:

| $R_1$ | $R_2$ | $R_3$ | $R_4$ | Yield (%) | M.P. (°C.) | Recrystallized from |
|---|---|---|---|---|---|---|
| —CH₃ | —CH₃ | —H | —H | 63 | 114–117 | Methanol |
| —CH₃ | —CH₃ | —CH₃ | —H | 41 | 132–134 | Ethanol |
| —CH₃ | —C₅H₉ (cyclopentyl) | —H | —H | 45.8 | 141–143 | Ethyl acetate/Ether |
| —C₅H₉ (cyclopentyl) | —CH₃ | —H | —H | 52 | 111–112.5 | Ethyl acetate/Ether |

EXAMPLE 3

5-(3-benzyloxy-4-methoxyphenyl)-2-oxazolidinone 88.3 mmol of 2-amino-1-(3-benzyloxy-4-methoxyphenyl)-ethanol is dissolved in 200 ml. of absolute tetrahydrofuran and combined under the exclusion of moisture with 92.6 mmol of carbonyl diimidazole. The clear solution is stirred overnight at room temperature. After removing the tetrahydrofuran by distillation, the mixture is taken up in 300 ml. of ethyl acetate, extracted twice with 1 N hydrochloric acid, and then washed neutral with saturated NaCl solution, dried, filtered, and concentrated.

Recrystallization from ethyl acetate produces a 66% yield of 5-(3-benzyloxy-4-methoxyphenyl)-2-oxazolidinone, m.p. 83°-91°.

EXAMPLE 4

5-(3-Hydroxy-4-methoxyphenyl)-2-oxazolidinone 40.6 mmol of 5-(3-benzyloxy-4-methoxyphenyl)-2-oxazolidinone is dissolved in 700 ml. of ethanol and hydrogenated in the presence of 8 g. of Raney nickel (B 113, Degussa company, Frankfurt) at room temperature under a hydrogen pressure of 100 atmospheres for a period of 2.2 hours. After the mixture has been filtered off from the catalyst, it is concentrated by evaporation, and the residue is recrystallized from methanol, thus obtaining 6.74 g. of 5-(3-hydroxy-4-methoxyphenyl)-2-oxazolidinone, m.p. 157°-160° (methanol).

EXAMPLE 5

5-(3-Cyclopentoxy-4-methoxyphenyl)-2-oxazolidinone 7.2 mmol of 5-(3-hydroxy-4-methoxyphenyl)-2-oxazolidinone is dissolved in 10 ml. of absolute dimethylformamide and stirred with 7.9 mmol of sodium hydride for 1 hour at 50°. After cooling, the mixture is combined with 8.6 mmol of cyclopentyl bromide and then agitated for 2 hours at 80°. After the reaction is terminated, the dimethylformamide is withdrawn under vacuum at 40°. The residue is taken up in 100 ml. of 2 N sodium hydroxide solution and extracted three times with 150 ml. of chloroform. The combined chloroform phases are washed with water, dried, filtered, and concentrated. The residue is recrystallized from ethyl acetate/ether, thus obtaining in a 70% yield 5-(3-cyclopentoxy-4-methoxyphenyl)-2-oxazolidinone, m.p. 111°-112°.

EXAMPLE 6

In accordance with the method described in Example 5, the compounds indicated in the following table ($R_3=R_4=H$) are produced from 5-(3-hydroxy-4-methoxyphenyl)-2-oxazolidinone and the halogenide or tosylate $R_1W$.

The abbreviations in the table mean the following:
DMF=dimethylformamide
Petr.=petroleum ether
$CHCl_3$=chloroform
Tos.=tosylate
NaH=sodium hydride
NaOEt=sodium ethylate

TABLE

| Solvent | $R_2$ | $R_1$ | W | Yield (%) | M.P. (°C.) | Recrystallized from | Temperature/Time |
|---|---|---|---|---|---|---|---|
| DMF/NaH | —$CH_3$ | —$CH_3$ | I | 60 | 114-117 | Methanol | 60° / 2 h |
| DMF/NaH | —$(CH_2)_2$—$CH_3$ | —$CH_3$ | Br | 64 | 98-100 | Ethyl acetate | 80° / 2 h |
| DMF/NaH | —$CH_2$—$CH(CH_3)_2$ | —$CH_3$ | Br | 34 | 107-110 | Ethyl acetate | 80° / 3 h |
| DMF/NaH | 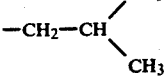 | —$CH_3$ | Br | 20 | 106-107 | Ethyl acetate | 60° / 20 h |
| DMF/NaH | $(CH_2)_3$—$CH_3$ | —$CH_3$ | Br | 43 | 74-75 | Ethyl acetate | 90° / 4.5 h |
| DMF/NaH | —$CH_2$—$CH=CH_2$ | —$CH_3$ | Br | 70 | 87-88 | Ethyl acetate/Petr. | 60° / 3 h |
| DMF/NaH | —$CH_2$—$C\equiv CH$ | —$CH_3$ | Br | 80 | 146-147 | Ethyl acetate/Petr. | 60° / 3 h |
| DMF/NaH | —$CH_2$—$C(CH_3)=CH_2$ | —$CH_3$ | Cl | 47 | Oil | Chromatography $CHCl_3$/Methanol (9:1) | 50° / 3 h |
| Ethanol/NaOEt |  | —$CH_3$ | I,Cl | 26 | 108-109 | Chromatography $CHCl_3$/Methanol and Ethyl acetate/Petr. | 70° / 6 h |
| DMF/NaH | 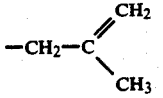 | —$CH_3$ | Tos. | 37 | 86-88 | Ethyl acetate | 90° / 3 h |

EXAMPLE 7

5-(3,4-Dimethoxyphenyl)-2-oxazolidinethione and 5-(3,4-Dimethoxyphenyl)-2-thiazolidinone 45 mmol of 2-amino-1-(3,4-dimethoxyphenyl)-ethanol is dissolved in 65 ml. of absolute dimethyl sulfoxide and combined in succession with 1.8 g. of pulverized potassium hydroxide and 1.4 ml. of carbon disulfide at 10°. The reaction mixture is then stirred under the exclusion of moisture for 2.5 hours. After withdrawing the dimethyl sulfoxide under vacuum, the residue is combined with 100 ml. of water and extracted three times with 100 ml. of chloroform. The combined chloroform phases are dried over anhydrous magnesium sulfate, filtered, and concentrated. The residue is chromatographed over 125 g. of silica gel with chloroform:methanol (96:4). After recrystallization of the corresponding fractions from methanol, a 9% yield of 5-(3,4-dimethoxyphenyl)-2-oxazolidinethione, m.p. 177°-178° is obtained in addition to a 6% yield of 5-(3,4-dimethoxyphenyl)-2-thiazolidinone, m.p. 167°-169°.

EXAMPLE 8

5-(3,4-Dimethoxyphenyl)-2-thiazolidinone 10 mmol of 2-amino-1-(3,4-dimethoxyphenyl)-ethanol is dissolved in 6 ml. of pyridine and, under cooling to 0°, combined dropwise with 11 mmol of carbon disulfide in 10 mmol of triethylamine. During this step, the temperature rises greatly. The mixture is agitated for one hour at 0° and then, at the same temperature, 10 mmol of benzyl chloride is added dropwise thereto. After agitation overnight at 0°, the batch is taken up in 40 ml. of 3 N sulfuric acid and extracted three times with respectively 50 ml. of chloroform. The combined chloroform phases are washed in succession with sodium bicarbonate and water, dried, filtered, and concentrated. The residue, which crystallizes spontaneously, is recrystallized from benzene and ethyl acetate, thus obtaining in a quantitative yield the benzyl ester of [2-(3,4-dimethoxyphenyl)-2-hydroxyethyl]-dithiocarbamic acid, m.p. 130°-132°.

At +5°, 2.14 mmol of phosphorus tribromide is added dropwise to 6.07 mmol of the benzyl ester of [2-(3,4-dimethoxyphenyl)-2-hydroxyethyl]-dithiocarbamic acid in 50 ml. of absolute ether. After agitating the batch for 20 hours at 5°, 10 ml. of methanol/water is added dropwise under cooling so that the temperature does not rise above 20°. The reaction mixture is then gently stirred into 20 ml. of sodium bicarbonate solution. The mixture is extracted three times with respectively 50 ml. of chloroform, and the combined organic phases are washed in succession with 50 ml. of sodium bicarbonate solution and 50 ml. of water, dried, filtered, and concentrated, thus obtaining in an 80% yield 2-benzylthio-5-(3,4-dimethoxyphenyl)-1,3-thiazol-2-ine as an oil.

This oil is dissolved in 20 ml. of ethanol, combined with 20 ml. of 6 N hydrochloric acid, and refluxed for 4 hours. After concentration, the residue is taken up in 25 ml. of ethanol, combined with 19 ml. of 1 N sodium hydroxide solution, and stirred for 3 hours at room temperature. The reaction mixture is then neutralized with 2 N hydrochloric acid, the ethanol is withdrawn, and the mixture is extracted three times with respectively 100 ml. of chloroform. The chloroform phase is washed with water, dried, and concentrated. The residue is chromatographed over 50 g. of silica gel with the eluent chloroform/methanol (96:4). The corresponding fractions are recrystallized from methanol, thus obtaining a 50% yield of 5-(3,4-dimethoxyphenyl)-2-thiazolidinone, m.p. 167°–169°.

EXAMPLE 9

5-(3,4-Dimethoxyphenyl)-2-oxazolidinone-3-carboxylic Acid Anilide 0.5 mmol of 5-(3,4-dimethoxyphenyl)-2-oxazolidinone is heated in 3 ml. of phenyl isocyanate for 3 hours to 160°. After cooling, the reaction mixture is concentrated under vacuum and chromatographed over 50 g. of silica gel with cyclohexane/ethyl acetate (1:1). After recrystallizing the corresponding fractions from ethyl acetate, a 60% yield of 5-(3,4-dimethoxyphenyl)-2-oxazolidinone-3-carboxylic acid anilide, m.p. 175°–182°, is obtained.

EXAMPLE 10

5-(3,4-dimethoxyphenyl)-2-oxazolidinone 100 mmol of 2-amino-1-(3,4-dimethoxyphenyl)-ethanol is dissolved in 100 ml. of chloroform. After cooling to 0°, a solution of 100 mmol of phosgene in 100 ml. of chloroform is added dropwise so slowly that the internal temperature does not rise above 5°. After one hour of agitation at 5°–10°, 200 mmol of pyridine in 100 ml. of chloroform is added dropwise to the reaction mixture, and the latter is stirred for 3 hours. After washing the organic phase in semisaturated NaCl solution, the mixture is concentrated by evaporation and recrystallized from methanol, thus obtaining in a 75% yield 5-(3,4-dimethoxyphenyl)-2-oxazolidinone, m.p. 114°–117°.

EXAMPLE 11

5-(3,4-Dimethoxyphenyl)-2-oxazolidinone 5 mmol of 2-amino-1-(3,4-dimethoxyphenyl)-ethanol is dissolved in 5 ml. of 2 N sodium hydroxide solution. The solution, cooled to 0°, is combined dropwise with 10 mmol of the ethyl ester of chloroformic acid. After the compound has been added, the mixture is stirred for 30 minutes at 0°. The thus-formed crystals are vacuum-filtered, washed with water, and dried, thus obtaining an 86% yield of 2-(3,4-dimethoxyphenyl)-2-hydroxyethylcarbamic acid ethyl ester, m.p. 90°–92°.

3 mmol of 2-(3,4-dimethoxyphenyl)-2-hydroxyethylcarbamic acid ethyl ester is suspended with 4 mmol of sodium methylate in 12 ml. of toluene and heated for 2 hours to a bath temperature of 110° under the exclusion of moisture. During this step, methanol and ethanol are distilled off. The toluene is then withdrawn under vacuum, the residue is taken up in 50 ml. of chloroform and distributed over 10 ml. of water. After drying, filtration, and concentration of the organic phase, the mixture is recrystallized from methanol, thus obtaining an 80% yield of 5-(3,4-dimethoxyphenyl)-2-oxazolidinone, m.p. 114°–117°.

EXAMPLE 12

3-Acetyl-5-(3,4-dimethoxyphenyl)-2-oxazolidinone 8.9 mmol of 5-(3,4-dimethoxyphenyl)-2-oxazolidinone is combined with 10 ml. of acetic anhydride and 5 ml. of pyridine and heated for 5 hours to 100°. After concentrating the reaction mixture, it is recrystallized from ethyl acetate, thus obtaining 3-acetyl-5-(3,4-dimethoxyphenyl)-2-oxazolidinone in a 73% yield, m.p. 175°–182°.

EXAMPLE 13

5-(3,4-Dimethoxyphenyl)-5-propyl-2-oxazolidinone 56 mmol of 3,4-dimethoxybutyrophenone and 61.4 mmol of trimethylsilyl cyanide are heated, with the addition of 200 mg.=627 mmol of anhydrous zinc iodide, for 4 hours to 90° under a nitrogen atmosphere and under the exclusion of moisture. The reaction mixture is taken up in 15 ml. of absolute tetrahydrofuran and added dropwise to a suspension of 60 mmol of lithium aluminum hydride in 35 ml. of absolute tetrahydrofuran, then heated under nitrogen for one hour to 60°, and the excess lithium aluminum hydride is destroyed by the dropwise addition of ethyl acetate and water. The precipitate is vacuum-filtered over silica gel, washed thoroughly with ethanol, and the mother liquor is concentrated. The residue is taken up in ethyl acetate, acidified with 4 N hydrochloric acid, and extracted. The aqueous phase is adjusted to pH 9 with sodium carbonate, saturated with sodium chloride, and extracted with chloroform. The chloroform phase is washed neutral with saturated sodium chloride solution, and the solvent is distilled off after drying over sodium sulfate, thus obtaining 5-amino-4-(3,4-dimethoxyphenyl)-4-pentanol in a 75.5% yield in the form of an oil. An analytical sample as the hydrochloride melts at 175°–176°.

17.35 mmol of 5-amino-4-(3,4-dimethoxyphenyl)-4-pentanol is dissolved in 10 ml. of absolute dimethylformamide and reacted with 18.3 mmol of 98% strength carbonyl diimidazole in 100 ml. of absolute tetrahydrofuran for 4 days at room temperature under the exclusion of moisture. After the solvent has been distilled off, the residue is taken up in ethyl acetate, extracted twice with 1 N hydrochloric acid, and washed neutral with saturated sodium chloride solution. The thus-obtained oil is purified by way of a silica gel column (350 g.) in a chloroform/methanol system 30:1. The product is 5-(3,4-dimethoxyphenyl)-5-propyl-2-oxazolidinone in an 81.7% yield in the form of an oil.

EXAMPLE 14

5-(3,4-Dimethoxyphenyl)-5-methyl-2-oxazolidinone

Analogously to Example 13, 3,4-dimethoxyacetophenone produces 5-(3,4-dimethoxyphenyl)-5-methyl-2-oxazolidinone in a total yield of 30%, m.p. 98°–101°.

EXAMPLE 15

5-(3,4-dimethoxyphenyl)-3-methyl-2-oxazolidinone 10 mmol of 5-(3,4-dimethoxyphenyl)-2oxazolidinone is dissolved in 20 ml. of absolute dimethylformamide and combined with 11 mmol of sodium hydride. The mixture is then stirred for 40 minutes at 40°. After cooling, 20 mmol of methyl iodide in 5 ml. of dimethylformamide is added dropwise and thereafter the reaction mixture is agitated for 6 hours at 50°. After the dimethylformamide has been removed by evaporation, the mixture is taken up in chloroform and then washed first with a small amount of water and then with saturated sodium chloride solution, dried, filtered, and concentrated. The residue is chromatographed over 60 g. of silica gel with chloroform/methanol (96:4) as the eluent. Recrystallization from ethanol produces a 60% yield of 5-(3,4-dimethoxyphenyl)-3-methyl-2-oxazolidinone, m.p. 132°–133°.

EXAMPLE 16

Benzyl Ester of 5-(3,4-Dimethoxyphenyl)-2-oxazolidinone-3-carboxylic Acid

6.25 mmol of 5-(3,4-dimethoxyphenyl)-2-oxazolidinone is dissolved in 30 ml. of dioxane and combined with 6.25 ml. (12.50 mmol) of a 2 N sodium hydroxide solution. At +4°, the batch is combined with 12.5 ml. of carbobenzoxy chloride and stirred for 4 hours at this temperature.

After the mixture has been combined with 50 ml. of 2 N sodium hydroxide solution, it is extracted three times with respectively 50 ml. of ethyl acetate. The ethyl acetate phase is washed once with 50 ml. of 2 N sodium hydroxide solution and twice with respectively 50 ml. of water, dried over "Sikkon," filtered, and concentrated. After the still remaining carbobenzoxy chloride has been evaporated at 100° and under 1 torr [mm. Hg], the residue is recrystallized from ethyl acetate/petroleum ether, producing a 64% yield of the benzyl ester of 5-(3,4-dimethoxyphenyl)-2-oxazolidinone-3-carboxylic acid, m.p. 124°–126°.

EXAMPLE 17

Ethyl Ester of 5-(3,4-Dimethoxyphenyl)-2-oxazolidinone-3-carboxylic Acid

5 mmol of 5-(3,4-dimethoxyphenyl)-oxazolidinone is combined in 20 ml. of toluene (absolute) with 10 mmol of triethylamine at 0° and under the exclusion of moisture. The batch is combined with 10 mmol of the ethyl ester of chloroformic acid, refluxed for 4 hours, and allowed to stand overnight. The thus-crystallized product is vacuum-filtered and then once again refluxed with 7.6 mmol of triethylamine and 7.6 mmol of the ethyl ester of chloroformic acid. The crystallized product is again vacuum-filtered; the combined filtrates are evaporated. Chromatography of the residue over 80 g. of silica gel with cyclohexane/ethyl acetate 1:1 as the eluent produces a 43% yield of 5-(3,4-dimethoxyphenyl)-2-oxazolidinone-3-carboxylic acid ethyl ester, m.p. 181°–185°.

EXAMPLE 18

Analogously to Example 15, the oxazolidinones listed in the table below are prepared from 5-(3,4-dimethoxyphenyl)-2-oxazolidinone:

| $R_1$ | $R_2$ | $R_3$ | $R_4$ | Yield (%) | M.P. (°C.) | Recrystallization from: |
|---|---|---|---|---|---|---|
| CH$_3$ | CH$_3$ | i-Propyl | H | 47 | 66–67 | Ethyl acetate/ Petroleum ether |
| CH$_3$ | CH$_3$ | —CH$_2$-φ | H | 66 | 75–76 | Ethyl acetate/ Petroleum ether |
| CH$_3$ | CH$_3$ | 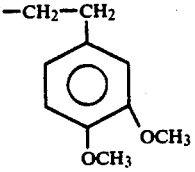 | H | 40 | 77–78 | Ethyl acetate/ Petroleum ether |

EXAMPLE 19

5-(3,4-Dimethoxyphenyl)-4-methyl-2-oxazolidinone

5.5 mmol of 2-amino-(3,4-dimethoxyphenyl)-propanol is dissolved in 50 ml. of chloroform and stirred with 1.05 g. (6.5 mmol) of carbonyl diimidazole for 2 hours under the exclusion of moisture. After allowing the reaction mixture to stand overnight, the mixture is extracted with the use of 50 ml. of distilled water, dried, filtered, and concentrated. After chromatography of the residue over 50 g. of silica gel with chloroform/methanol (95:5) as the eluent and recrystallization from ethyl acetate/petroleum ether, a 24% yield is obtained of 5-(3,4-dimethoxyphenyl)-4-methyl-2-oxazolidinone, m.p. 98°–99°.

The starting material, 2-amino-1-(3,4-dimethoxy)-propanol, is prepared as follows:

10 ml. of sulfuryl chloride in 80 ml. of methylene chloride is added dropwise at room temperature to 100 mmol of 3,4-dimethoxypropiophenone in 160 ml. of methylene chloride. The mixture is then agitated at room temperature for 3.5 hours. After withdrawing the solvent and recrystallizing the residue from cyclohexane/petroleum ether, an 89% yield of 2'-chloro-3,4-dimethoxypropiophenone is obtained, m.p. 56°–57°.

Under the exclusion of moisture, 43.86 mmol of 2'-chloro-3,4-dimethoxypropiophenone, dissolved in 230 ml. of acetone, is agitated for 7 days with 437 mg. of potassium iodide and 87.72 mmol of dibenzylamine. The batch is diluted with diethyl ether to form a 1 liter solution, and then filtered and concentrated. The residue is applied to silica gel, and the silica gel is first extracted with chloroform and then with ethanol, in each case conducting a vacuum-filtering step. The chloroform phase is chromatographed over 500 g. of silica gel with chloroform as the eluent, producing a 49% yield of 2'-N,N-dibenzylamino-3,4-dimethoxypropiophenone as an oil.

12.39 g. (31.8 mmol) of 2'-N,N-dibenzylamino-3,4-dimethoxypropiophenone is dissolved in 75 ml. of isopropanol and combined with 1.33 g. (35.05 mmol) of sodium boranate. After one hour of agitation at room temperature, the mixture is heated under reflux for 2 hours. After cooling, the batch is vacuum-filtered, and the residue is extracted under boiling with ethyl acetate. Filtration yields a crystallized product in a 59% yield, namely 2'-(N,N-dibenzylamino)-1-(3,4-dimethoxyphenyl)-propanol, m.p. 151°-152°.

13.2 mmol of the dibenzyl compound is hydrogenated in 50 ml. of ethanol (p.a.) [=pro analysis] with 2.64 g. of palladium/charcoal (10%) for 3 hours at 90° under a hydrogen pressure of 10 atmospheres gauge. After the mixture has been vacuum-filtered, it is concentrated and recrystallized from ethanol, resulting in a 64% yield of 2-amino-1-(3,4-dimethoxyphenyl)-propanol, m.p. 131°-132°.

EXAMPLE 20

Ethyl Ester of 5-(3,4-Dimethoxyphenyl)-2-oxo-oxazolidine-4-carboxylic Acid 6 mmol of 2-amino-4-(3,4-dimethoxyphenyl)-3-hydroxypropionic acid ethyl ester is stirred with 12 mmol of carbonyl diimidazole in 60 ml. of chloroform for 4 hours at room temperature under the exclusion of moisture. The mixture is then extracted once against 50 ml. of water, dried overnight over silica gel, filtered, and concentrated.

The residue is chromatographed over 130 g. of silica gel with chloroform/methanol (90:10) as the eluent. Recrystallization from ethyl acetate/ethanol results in a 34% yield of 5-(3,4-dimethoxyphenyl)-2-oxo-oxazolidinone-4-carboxylic acid ethyl ester, m.p. 188°-189°.

The starting material, the ethyl ester of 2-amino-4-(3,4-dimethoxyphenyl)-3-hydroxypropionic acid, is prepared as follows:

44.37 mmol of the ethyl ester of 3,4-dimethoxyglycidic acid (prepared according to W. Schneider et al., Arch. Pharm. 299:817 [1966]) is refluxed with 97.61 mmol of dibenzylamine in 100 ml. of ethanol for 4.5 hours under the exclusion of moisture. After allowing the reaction mixture to stand for 3 days at room temperature, the batch is concentrated, and the residue is chromatographed over 400 g. of silica gel with chloroform/methanol (98:2) as the eluent. A repetition of the chromatography of the correspondingly combined fractions results in an 89% yield of 2-N,N-dibenzylamino-4-(3,4-dimethoxyphenyl)-3-hydroxypropionic acid ethyl ester in the form of an oil.

22.2 mmol of 2-N,N-dibenzylamino-4-(3,4-dimethoxyphenyl)-3-hydroxypropionic acid ethyl ester is hydrogenated with 4.44 g. of palladium/charcoal (10%) in 100 ml. of nondenaturated ethanol for 3 hours at 90° and under a hydrogen pressure of 10 atmospheres gauge. After the mixture has been vacuum-filtered off from the catalyst, it is concentrated. Recrystallization from nondenaturated ethanol produces an 80% yield of the ethyl ester of 2-amino-4-(3,4-dimethoxyphenyl)-3-hydroxypropionic acid, m.p. 211°-212° (decomposition).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 5-(substituted phenyl)-oxazolidinone and its sulfur analog of the Formula

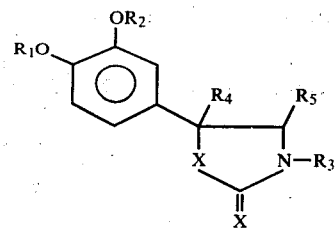

wherein
$R_1$ is lower alkyl, $C_{3-7}$ cycloalkyl or $C_{3-7}$ cycloalkylalkyl;
$R_2$ is hydrogen, lower alkyl, $C_{3-7}$ cycloalkyl, $C_{3-7}$ cycloalkylalkyl, aryl, ar-$C_{1-4}$ alkyl, $C_{2-5}$ alkenyl, 2- or 3-tetrahydrofuranyl, 2- or 3-tetrahydrothienyl or 2-tetrahydropyranyl;
$R_3$ is hydrogen, lower alkyl, $C_{2-5}$ alkenyl, $C_{2-5}$ alkynyl, aryl, ar-$C_{1-4}$-alkyl, or acyl
$R_4$ is hydrogen or lower alkyl;
$R_5$ is hydrogen, lower alkyl, or lower alkoxycarbonyl; and
X is oxygen or sulfur; and
wherein "lower" refers to 1-6 carbon atoms; and aryl and ar- are each phenyl or naphthyl.

2. 5-(3-Benzyloxy-4-methoxyphenyl)-2-oxazolidinone, a compound of claim 1.

3. 5-(3,4-Dimethoxyphenyl)-2-oxazolidinone, a compound of claim 1.

4. 3-Methyl-5-(3,4-dimethoxyphenyl)-2-oxazolidinone, a compound of claim 1.

5. 5-(3-Methoxy-4-cyclopentoxyphenyl)-2-oxazolidinone, a compound of claim 1.

6. 5-(3-Cyclopentoxy-4-methoxyphenyl)-2-oxazolidinone, a compound of claim 1.

7. 5-(3-Hydroxy-4-methoxyphenyl)-2-oxazolidinone, a compound of claim 1.

8. 5-(3-Propoxy-4-methoxyphenyl)-2-oxazolidinone, a compound of claim 1.

9. 5-(3-Isobutoxy-4-methoxyphenyl)-2-oxazolidinone, a compound of claim 1.

10. 5-(3-Cyclobutoxy-4-methoxyphenyl)-2-oxazolidinone, a compound of claim 1.

11. 5-(3-n-Butoxy-4-methoxyphenyl)-2-oxazolidinone, a compound of claim 1.

12. 5-(3-Allyloxy-4-methoxyphenyl)-2-oxazolidinone, a compound of claim 1.

13. 5-(3-Propargyloxy-4-methoxyphenyl)-2-oxazolidinone, a compound of claim 1.

14. 5-(3-Methylallyloxy-4-methoxyphenyl)-2-oxazolidinone, a compound of claim 1.

15. 5-(3-Phenyloxy-4-methoxyphenyl)-2-oxazolidinone, a compound of claim 1.

16. 5-[3-(3-Tetrahydrofuranyloxy)-4-methoxyphenyl]-2-oxazolidinone, a compound of claim 1.

17. 5-(3,4-Dimethoxyphenyl)-2-oxazolidinethione, a compound of claim 1.

18. 5-(3,4-Dimethoxyphenyl)-2-thiazolidinone, a compound of claim 1.

19. 5-(3,4-Dimethoxyphenyl)-2-oxazolidinone-3-carboxylic acid anilide, a compound of claim 1.

20. 3-Acetyl-5-(3,4-dimethoxyphenyl)-2-oxazolidinone, a compound of claim 1.

21. 5-(3,4-Dimethoxyphenyl)-5-methyl-2-oxazolidinone, a compound of claim 1.

22. 5-(3,4-Dimethoxyphenyl)-5-propyl-2-oxazolidinone, a compound of claim 1.

23. Benzyl ester of 5-(3,4-dimethoxyphenyl)-2-oxazolidinone-3-carboxylic acid, a compound of claim 1.

24. Ethyl ester of 5-(3,4-dimethoxyphenyl)-2-oxazolidinone-3-carboxylic acid, a compound of claim 1.

25. 5-(3,4-Dimethoxyphenyl)-3-isopropyl-2-oxazolidinone, a compound of claim 1.

26. 5-(3,4-Dimethoxyphenyl)-3-benzyl-2-oxazolidinone, a compound of claim 1.

27. 5-(3,4-Dimethoxyphenyl)-3-(3,4-dimethoxyphenylethyl)-2-oxazolidinone, a compound of claim 1.

28. 5-(3,4-Dimethoxyphenyl)-4-methyl-2-oxazolidinone, a compound of claim 1.

29. Ethyl ester of 5-(3,4-dimethoxyphenyl)-2-oxooxazolidine-4-carboxylic acid, a compound of claim 1.

* * * * *